US00PP31241P2

(12) United States Plant Patent
Zeng et al.

(10) Patent No.: US PP31,241 P2
(45) Date of Patent: Dec. 17, 2019

(54) ***NELUMBO* PLANT NAMED 'CENGHONG DINGCUI'**

(50) Latin Name: *Nelumbo nucifera*
Varietal Denomination: Cenghong Dingcui

(71) Applicants: Xianbao Zeng, Hangzhou (CN); Yan Shen, Hangzhou (CN)

(72) Inventors: Xianbao Zeng, Hangzhou (CN); Yan Shen, Hangzhou (CN)

(73) Assignee: Zhejiang Renwen Landscape Architecture Co., Ltd., Hangzhou (CN)

( * ) Notice: Subject to any disclaimer, the term of this patent is extended or adjusted under 35 U.S.C. 154(b) by 0 days.

(21) Appl. No.: 16/350,034

(22) Filed: Sep. 17, 2018

(51) Int. Cl.
*A01H 5/02* (2018.01)

(52) U.S. Cl.
USPC ..... Plt./342

(58) Field of Classification Search
USPC ..... Plt./342
CPC ..... A01H 6/00; A01H 5/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Nelumbo* plant named 'Cenghong Dingcui', characterized by its upright plant habit; moderately vigorous growth habit; large medium green-colored leaves; freely flowering habit; and large red purple and lighter red purple bi-colored globose-shaped flowers that are positioned above the foliar plane on moderately strong and erect peduncles.

2 Drawing Sheets

Botanical designation: *Nelumbo nucifera.*
Cultivar denomination: 'CENGHONG DINGCUI'.

BACKGROUND OF THE INVENTION

The present invention relates to a new and distinct cultivar of *Nelumbo* plant, botanically known as *Nelumbo nucifera*, commonly referred to as Sacred or Indian Lotus, and hereinafter referred to by the name 'Cenghong Dingcui'.

The new *Nelumbo* plant is a product of a controlled breeding program conducted by the Inventors in Hangzhou, Zhejiang, China. The objective of the breeding program is to create new *Nelumbo* plants that have attractive and unique flower forms and flower colors.

The new *Nelumbo* plant originated from a cross-pollination in July, 2014 of *Nelumbo nucifera* 'Zi Zhu', not patented, as the female, or seed, parent with *Nelumbo nucifera* 'Jin Pingguo', not patented, as the male, or pollen, parent. The new *Nelumbo* plant was discovered and selected by the Inventors as a single flowering plant within the progeny of the stated open-pollination in a controlled greenhouse environment in Hangzhou, Zhejiang, China in July, 2016.

Asexual reproduction of the new *Nelumbo* plant by rhizome divisions in a controlled environment in Hangzhou, Zhejiang, China since April, 2017 has shown that the unique features of this new *Nelumbo* plant are stable and reproduced true to type in successive generations of asexual reproduction.

SUMMARY OF THE INVENTION

Plants of the new *Nelumbo* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cenghong Dingcui'. These characteristics in combination distinguish 'Cenghong Dingcui' as a new and distinct *Nelumbo* plant:

1. Upright plant habit.
2. Moderately vigorous growth habit.
3. Large medium green-colored leaves.
4. Freely flowering habit.
5. Large red purple and lighter red purple bi-colored globose-shaped flowers that are positioned above the foliar plane on moderately strong and erect peduncles.

Plants of the new *Nelumbo* differ from plants of the female parent, 'Zi Zhu', in the following characteristics:

1. Flowers of plants of the new *Nelumbo* are globose-shaped whereas flowers of plants of 'Zi Zhu' are bowl-shaped.
2. Flowers of plants of the new *Nelumbo* have 15 times as many petals and petaloids as flowers of plants of 'Zi Zhu'.

Plants of the new *Nelumbo* differ from plants of the male parent, 'Jin Pingguo', in the following characteristics:

1. Flowers of plants of the new *Nelumbo* are globose-shaped whereas flowers of plants of 'Jin Pingguo' are bowl-shaped.
2. Flowers of plants of the new *Nelumbo* have bi-colored petals and petaloids whereas petals and petaloids of flowers of plants of 'Jin Pingguo' are not bi-colored.

Plants of the new *Nelumbo* can be compared to plants of *Nelumbo nucifera* 'Hongyan Sanbaichong', not patented. In side-by-side comparisons plants of the new *Nelumbo* differ primarily from plants of 'Hongyan Sanbaichong' in the following characteristics:

1. Flowers of plants of the new *Nelumbo* are ball-shaped whereas flowers of plants of 'Hongyan Sanbaichong' are plate-shaped.
2. Plants of the new *Nelumbo* have larger flowers than plants of 'Hongyan Sanbaichong'.
3. Flowers of plants of the new *Nelumbo* have red purple and lighter red purple bi-colored petals and petaloids whereas petals and petaloids of flowers of plants of 'Hongyan Sanbaichong' are light red purple in color and not bi-colored.

BRIEF DESCRIPTION OF THE PHOTOGRAPHS

The accompanying photographs illustrate the overall appearance of the new *Nelumbo* plant showing the colors as true as it is reasonably possible to obtain in colored reproductions of this type. Colors in the photographs may differ slightly from the color values cited in the detailed botanical description which accurately describe the colors of the new *Nelumbo* plant.

The photograph on the first sheet is a side perspective view of a typical plant of 'Cenghong Dingcui' grown in a container.

The photograph on the second sheet is a close-up view of a typical flower of 'Cenghong Dingcui'.

DETAILED BOTANICAL DESCRIPTION

The aforementioned photographs and following observations and measurements describe plants grown during the summer in 37-cm by 30-cm containers in an outdoor nursery in Hangzhou, Zhejiang, China and under cultural practices typical of commercial *Nelumbo* production. During the production of the plants, day temperatures ranged from 14° C. to 33° C. and night temperatures ranged from 16° C. to 28° C. Plants were one year old when the photographs and the detailed description were taken. In the following description, color references are made to The Royal Horticultural Society Colour Chart, 2007 Edition, except where general terms of ordinary dictionary significance are used.

Botanical classification: *Nelumbo nucifera* 'Cenghong Dingcui'.

Parentage:

*Female, or seed, parent.*—*Nelumbo nucifera* 'Zi Zhu', not patented.

*Male, or pollen, parent.*—*Nelumbo nucifera* 'Jin Pingguo', not patented.

Propagation:

*Type.*—By rhizome divisions.

*Time to initiate roots, summer.*—About four days at temperatures about 27° C.

*Time to produce a rooted young plant.*—About seven days at temperatures about 27° C.

*Root description.*—Fine, fleshy; typically white to grey brown in color, actual color of the roots is dependent on water quality, fertilizer type and formulation, substrate temperature and physiological age of roots.

*Rooting habit.*—Not freely branching, medium density.

Plant description:

*Plant and growth habit.*—Upright plant habit; moderately vigorous growth habit and moderate growth rate.

*Plant height (soil level to top of foliar plane).*—About 84 cm.

*Plant height (soil level to top of floral plane).*—About 123 cm.

*Plant diameter.*—About 140 cm by 110 cm.

Rhizome description:

*Arrangement and habit.*—Sympodial branching habit with about nine to twelve primary branches developing per plant each with about 6.7 secondary branches.

*Length.*—About 80 cm to 190 cm.

*Diameter.*—About 1.5 cm to 4.3 cm.

*Internode length.*—About 9.3 cm to 36 cm.

*Texture and luster.*—Smooth, glabrous; glossy.

*Color.*—White, close to 159B.

Leaf description:

*Length, fully expanded.*—About 39 cm to 46 cm.

*Width, fully expanded.*—About 21 cm to 36 cm.

*Shape.*—Peltate, elliptical.

*Apex.*—Retuse.

*Base.*—Cuneate.

*Margin.*—Entire; undulate.

*Venation.*—Palmate.

*Texture and luster, upper and lower surfaces.*—Pubescent, papery; moderately glossy.

*Color.*—Developing leaves, upper surface: Close to 143A. Developing leaves, lower surface: Close to 138C. Fully expanded leaves, upper surface: Close to 137A; venation, close to 143A. Fully expanded leaves, lower surface: Close to 138B; venation, close to 145A.

*Petioles.*—Length: About 71 cm. Diameter: About 5 mm to 12 mm. Strength: Moderately strong. Texture and luster, upper and lower surfaces: Smooth, glabrous; moderately glossy. Color: Close to 145C.

Inflorescence description:

*Arrangement.*—Double-type globose-shaped flowers developing directly from the rhizomes with numerous showy petals and petaloids; about eight flower buds and flowers developing per plant at one time.

*Time to flower.*—In China, plants flower from June to August; flowering continuous during this period; flowers begin opening at 05:00 hours in the morning, flowers are fully opened at about 06:30 hours and are typically closed by 09:00 hours.

*Flower longevity.*—Flowers last about five days on the plant; flowers last about three days as a cut flower; flowers persistent; plants maintain good substance for about 45 days.

*Fragrance.*—Initially, very faint and then not detectable.

*Flower buds.*—Length: About 7.8 cm. Diameter: About 7.5 cm. Shape: Broadly ovate. Texture and luster: Smooth, glabrous; matte. Color: Close to 73B.

*Flowers.*—Shape and arrangement: Double-type, globose-shaped with numerous showy petals and petaloids. Diameter: About 18 cm. Height: About 12 cm.

*Petals.*—Quantity and arrangement: About 368 arranged in numerous whorls. Length: About 9.3 cm. Width: About 4.6 cm. Shape: Obovate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening and fully opened, upper surface: Distally, close to 59C; mid-section and towards the base, close to 69D; at the base, close to 6D; venation, close to 65B; color becoming closer to 70B with development. When opening and fully opened, lower surface: Distally, close to 59C; mid-section and towards the base, close to 63D; at the base, close to 4D; venation, close to 63B; color becoming closer to 64C with development.

*Petaloids*.—Quantity and arrangement: About 302 arranged in numerous whorls. Length: About 4.7 cm. Width: About 1.1 cm. Shape: Lanceolate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening and fully opened, upper surface: Distally, close to 59C; mid-section and towards the base, close to 69D; at the base, close to 6D; venation, close to 65B; color becoming closer to 70B with development. When opening and fully opened, lower surface: Distally, close to 59C; mid-section and towards the base, close to 63D; at the base, close to 4D; venation, close to 63B; color becoming closer to 64C with development.

*Sepals*.—Quantity and arrangement: About seven in a single whorl. Length: About 5.7 cm. Width: About 4.8 cm. Shape: Obovate. Apex: Acuminate. Base: Cuneate. Texture and luster, upper and lower surfaces: Smooth, glabrous; matte. Color: When opening and fully opened, upper surface: Close to 65D. When opening and fully opened, lower surface: Close to 65C.

*Peduncles*.—Length: About 114 cm. Diameter: About 2.1 cm. Strength: Moderately strong. Aspect: Mostly erect. Texture and luster: Smooth, glabrous; slightly glossy. Color: Close to 138B.

*Stamens*.—Quantity per flower: About 22. Filament length: About 1.4 cm. Filament color: Close to 4C. Anther length: About 1.3 cm. Anther width: About 1 mm. Anther shape: Lanceolate. Anther color: Close to 6C. Pollen amount: Moderate. Pollen color: Close to 6C.

*Pistils*.—Quantity per flower: About 26. Pistil length: About 3.8 cm. Style length: About 3.5 cm. Style color: Close to 7A. Stigma diameter: About 1 mm. Stigma shape: Rounded. Stigma color: Close to 7B. Ovary color: Close to 144A.

*Fruits and seeds*.—To date, fruit and seed development has not been observed on plants of the new *Nelumbo*.

Pathogen & pest resistance: To date, plants of the new *Nelumbo* have not been observed to be resistant to pathogens or pests common to *Nelumbo* plants.

Temperature tolerance: Plants of the new *Nelumbo* have been observed to be tolerant to temperatures ranging from about −5° C. to about 41° C.

It is claimed:

1. A new and distinct *Nelumbo* plant named 'Cenghong Dingcui' as illustrated and described.

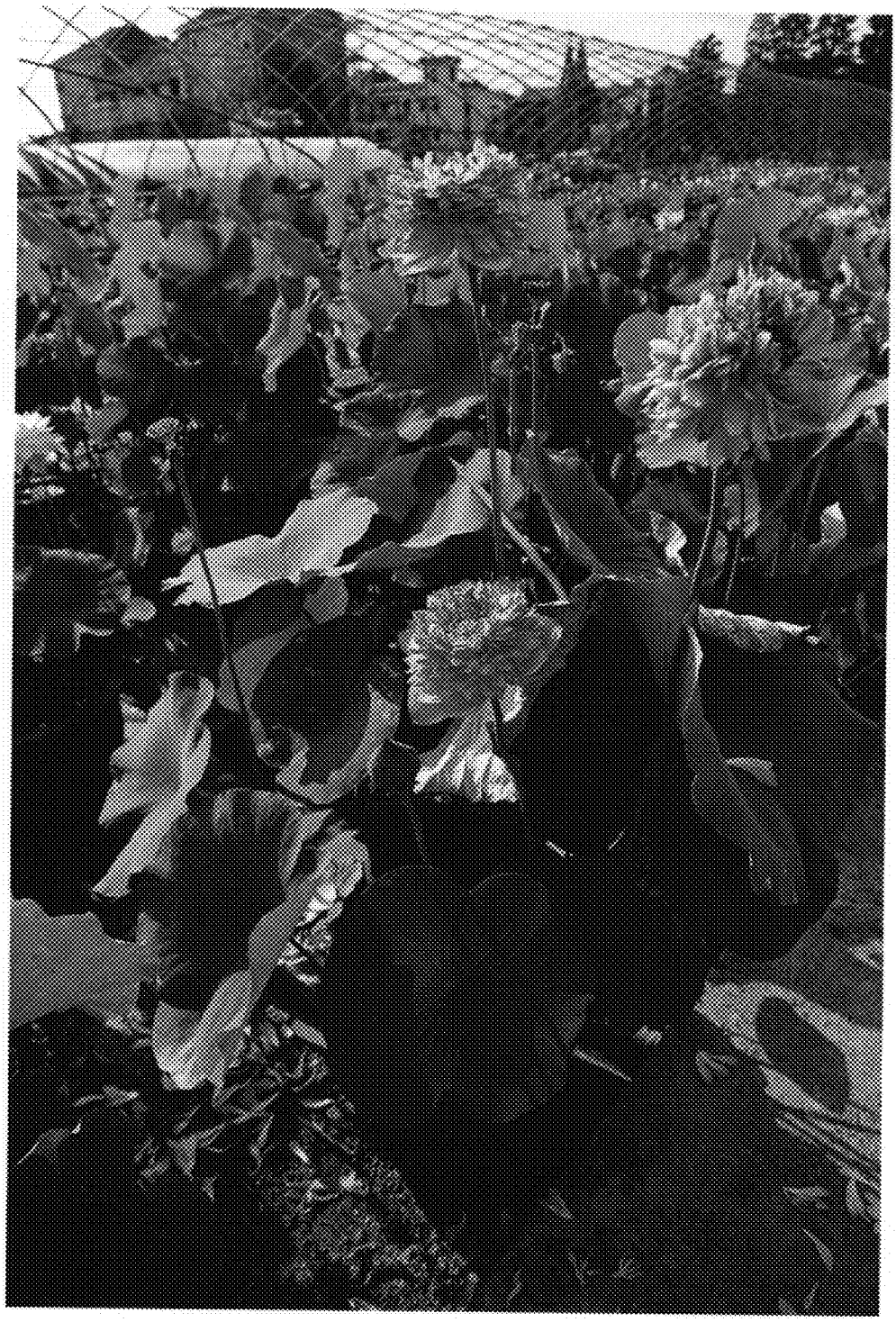

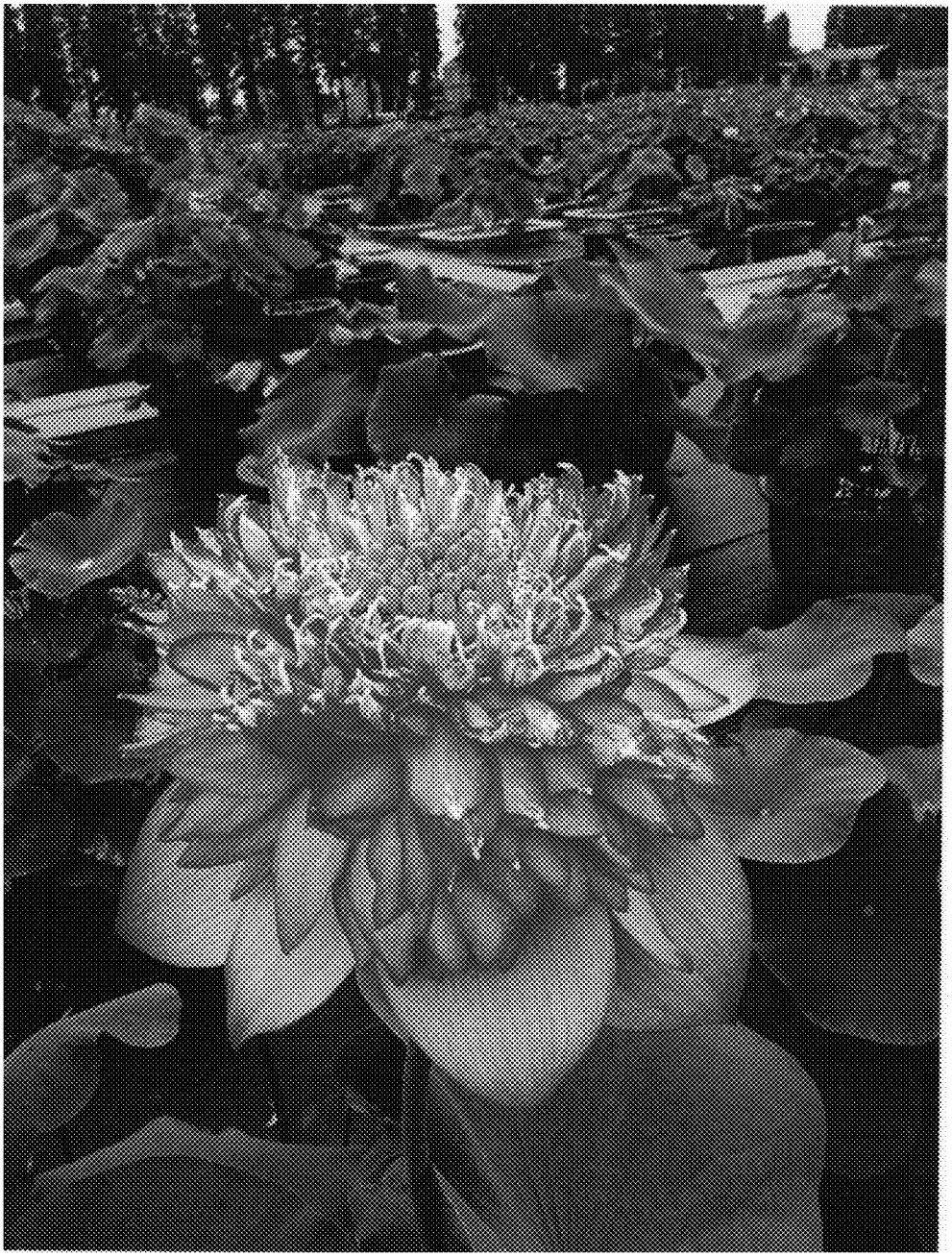

* * * * *